(12) United States Patent
Diesso

(10) Patent No.: US 6,352,585 B1
(45) Date of Patent: Mar. 5, 2002

(54) GYPSUM CASTING COMPOSITION AND METHOD OF CASTING

(76) Inventor: Michael Diesso, 14 Kendrick Rd., Wareham, MA (US) 02571

( * ) Notice: Subject to any disclaimer, the term of this patent is extended or adjusted under 35 U.S.C. 154(b) by 0 days.

(21) Appl. No.: 09/534,138

(22) Filed: Mar. 23, 2000

Related U.S. Application Data

(60) Provisional application No. 60/128,961, filed on Apr. 12, 1999.

(51) Int. Cl.[7] .................................................. C09K 3/00
(52) U.S. Cl. .......................... 106/35; 106/778; 106/772; 106/782; 106/785; 106/783; 106/787; 206/63.5; 433/214; 433/213
(58) Field of Search .......................... 206/63.5; 106/35, 106/778, 772, 782, 785, 783, 787; 433/214, 213

(56) References Cited

U.S. PATENT DOCUMENTS

| | | | |
|---|---|---|---|
| 2,046,366 A | * 7/1936 | Collins | 206/63.5 |
| 3,407,924 A | * 10/1968 | Lewis et al. | 206/63.5 |
| 3,598,621 A | * 8/1971 | Ferrara et al. | 106/778 |
| 3,610,586 A | * 10/1971 | Prince et al. | 206/63.5 |
| 3,958,997 A | 5/1976 | Greenberg | 249/105 |
| 3,989,220 A | 11/1976 | Greenberg | 206/63.5 |
| 4,094,693 A | * 6/1978 | Knorre et al. | 106/778 |
| 4,148,660 A | 4/1979 | Lankard et al. | 106/38.3 |
| 4,196,008 A | 4/1980 | Kennedy et al. | 106/115 |
| 4,268,310 A | 5/1981 | Nemeth | 106/38.35 |
| 4,299,790 A | 11/1981 | Greenberg | 264/299 |
| 4,526,619 A | * 7/1985 | Ohi et al. | 106/35 |
| 4,543,372 A | 9/1985 | Watanabe et al. | 523/109 |
| 4,670,053 A | 6/1987 | Kooke et al. | 106/35 |
| 4,762,561 A | 8/1988 | Holub et al. | 106/89 |
| 4,909,847 A | * 3/1990 | Ohi et al. | 106/38.35 |
| 4,911,759 A | * 3/1990 | Ohi et al. | 106/111 |
| 5,026,428 A | * 6/1991 | Cook | 106/38.3 |
| 5,052,554 A | 10/1991 | Leonard | 206/219 |
| 5,465,833 A | 11/1995 | Tarter | 206/63.5 |
| 5,560,774 A | 10/1996 | Burge et al. | 106/692 |
| 5,618,105 A | 4/1997 | Baker | 366/136 |
| 5,698,610 A | 12/1997 | Futami et al. | 523/109 |
| 5,709,467 A | 1/1998 | Galliano II | 366/130 |
| 5,743,431 A | 4/1998 | Brattesani | 222/1 |

OTHER PUBLICATIONS

Derwnet abstract for SU 1,426,959, Sep. 30, 1988.*

* cited by examiner

Primary Examiner—C. Melissa Koslow
(74) Attorney, Agent, or Firm—Robert F. I. Conte; Lee, Mann, Smith, McWilliams, Sweeney & Ohlson

(57) ABSTRACT

A multipart gypsum casting composition comprising a gypsum composition and a water composition where either the water and/or the gypsum composition contains at least two acids selected from the group consisting of oxalic acid, boric acid, phosphoric acid, citric acid, sodium citric acid, trisodium citric acid, tartaric acid, sulfuric acid, acetic acid, formic acid, malic acid, ascorbic acid and aspartic acid.

11 Claims, 2 Drawing Sheets

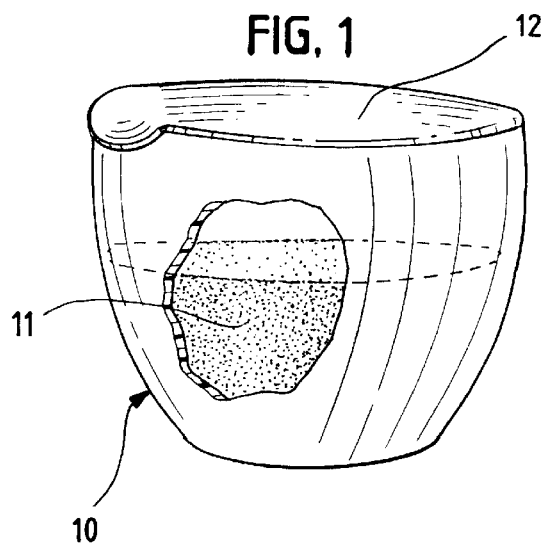
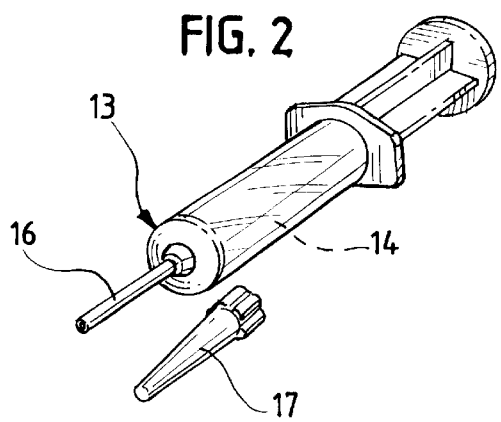
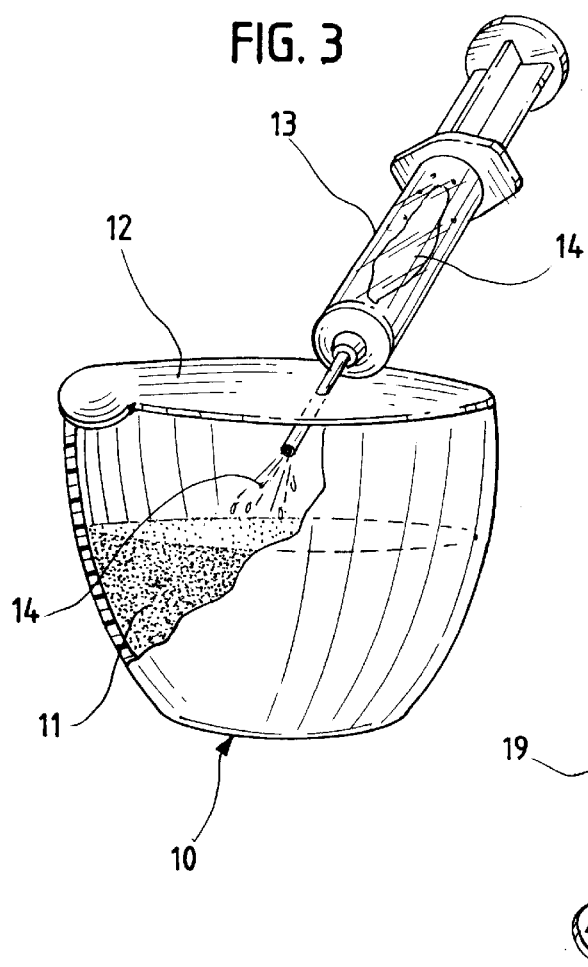
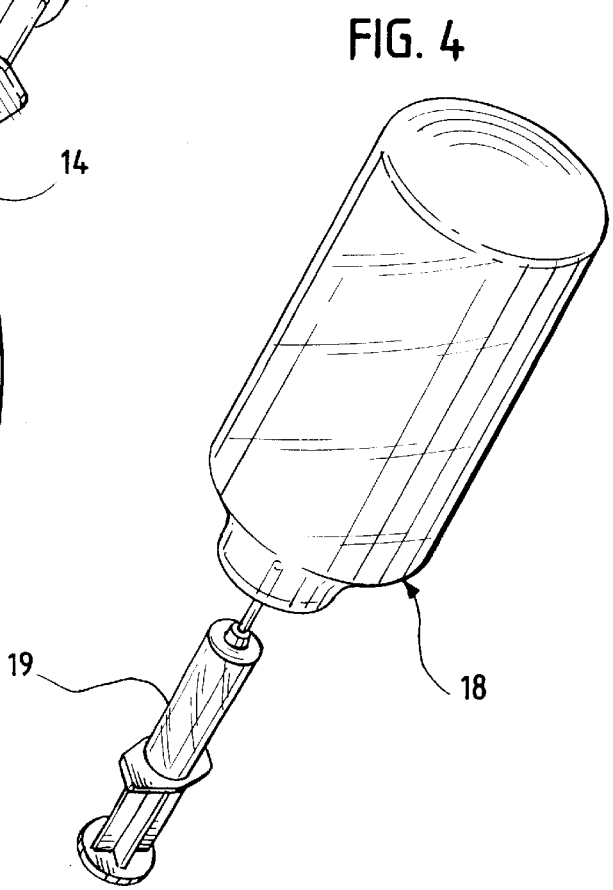

GYPSUM CASTING COMPOSITION AND METHOD OF CASTING

This application claims benefit of provisional application No. 60/128,961, filed Apr. 12, 1999

FIELD OF THE INVENTION

The present invention relates to a gypsum castings composition and casting method. More particularly, this invention relates to a gypsum casting composition which is particularly useful as a gypsum dental casting and to a method for producing gypsum dental or similar castings.

For the purpose of the present invention, gypsum and gypsum compositions are defined as materials that are chemically structured as or with calcium sulfates ($CaSO_4$), calcium sulfate dehydrate, calcinated calcium sulfate, or calcium sulfate hemihydrate as a reactive, setting or hardening component. They that are supplied as dry powders and are intended to be mixed with water to a slurry consistency and react with the water to harden into a set mass, mold or casting.

Gypsum for use in the production of castings is traditionally supplied as a dry powder that is extremely hygroscopic.

Dry gypsum powders intended for use in making gypsum dental castings are traditionally supplied as packaged in paper or plastic bags or corrugated boxes or fiber pails etc. in weight volumes of 25, 50, or 100 pounds and sometimes lesser quantities. For example, in one of the more prevalent methods for making gypsum dental castings the gypsum work area is located adjacent to a sink. The gypsum powder is transferred from its bulk package container to a plaster bin where it is stored and may be readily available. The process of transfer requires lifting a heavy weight package and then a messy, dusty task of emptying the dry powder into a storage bin. This transfer of gypsum powder to the storage bin releases dust into the surrounding air and causes cleanup requirements throughout the office. The dust also settles and in time absorbs moisture from the air thereby setting and clogging vents, cabinets, latches, control panels, dials, door hinges, and all nearby mechanical and electrical appliances and components.

The storage bin is traditionally compartmented to accommodate 25 to 50 lbs. of dental plaster, 25 to 50 lbs. of dental stone, and 25 to 50 lbs of dental die stone. These are different types of calcium sulfate hemihydrate determined by the temperature and method of calcining by a manufacturer.

Each type offers a different degree of hardness or set expansion. The transfer process is repeated each time one type of gypsum is emptied and needs replenishment.

To make a gypsum dental casting, the cover to the bin is opened and a measure of gypsum is removed and placed into a container on a weight scale. The amount is adjusted to a pre-determined weight. A measure of liquid is then placed into a measuring beaker. Manufacturers recommend a suggested liquid/powder ratio to achieve a pre-determined specification for set time, controlled expansion and hardness. Excess or insufficient liquid in the mix may affect the physical properties of the set casting. In practice however, the gypsum worker routinely desires to alter the physical properties of set time, hardness or expansion. This is time consuming, requires additional items of preparation such as a scale and a beaker, and increases the amount of gypsum dust that is dispersed into the air and spilled onto and around the work area. Extra cleanup time is additionally required for each of the items in use and the general cleanup of the work area.

The weighed gypsum powder and measured liquid is then transferred to a stiff rubber or vinyl mixing bowl. Mixing bowls are the preferred vessels for the preparation of gypsum and consistently produce predictable results. For general and routine small batch mixes, a stiff bladed spatula is used for the required vigorous stirring of the gypsum until a creamy paste/slurry is achieved. For large batches, a mechanical mixer/bowl device is recommended. The manipulation and transfer of gypsum powder to the mixing bowl further releases dust into the surrounding air. In effect every time the gypsum bin is opened, every time gypsum is transferred to a weight scale and every time gypsum is transferred to a mixing vessel, the powder dust is released into the surrounding air.

When the gypsum powder and the water are mixed to a slurry they are poured into a mold and allowed to set. All of the items used in the preparation of the mix are soiled with gypsum paste and must then be washed. This is the reason that gypsum work areas are traditionally located adjacent to a sink. This then creates an additional problem. The constant washing of gypsum items causes gypsum to build up in the pipes, plumbing and drains of the sink. Most gypsum work area sinks must be equipped with plaster traps that require frequent cleaning or plumbing repairs.

When the gypsum casting is set and returned to its dehydrate the problems of handling are still not ended. When the dry gypsum powder is mixed with water and allowed to set into a casting, the resulting casting is physically a reconfiguration of the original gypsum as mined. Gypsum is well known to have a characteristically, dry, chalky surface. Handling of the finished castings by workers has an irritating effect on the skin of the gypsum workers causing a drying and chaffing. In effect, it is the surface of the gypsum dusting off, through handling. This chalky surface is also traditionally weak and scratches easily producing more dust.

Attempts to reduce the problem of dust by formulating gypsums with various chemical additives have been disclosed such as in U.S. Pat. Nos. 4,911,759, 4,670,053, 5,698,610, 4,909,847 and 4,543,372. There has been little if any improvements utilizing these methods. Dust and mess continue to be a problem. Mixing bowls and utensils still need to be washed and sinks continue to be clogged.

U.S. Pat. Nos. 5,709,467, 5,618,105, 5,465,833 and 5,052,554 disclose a method of mixing gypsum compositions in a disposable plastic bag that is flexible and allows the gypsum mix to be kneaded. The physical constraints of a flexible bag and the kneading method prevent the gypsum from being vigorously stirred or agitated, as is usually required for dental castings. In addition once the bag is filled, water added and kneaded, its jelly-like form is difficult to properly manipulate and to portion out the slurry by squeezing and continual readjustment with one hand while holding and vibrating a mold with the other hand. The larger the bag the more difficult it becomes. The bag mixing techniques additionally makes it difficult for a worker to use a spatula to scoop out a portion of the paste mix and place it onto or into specific areas for shaping or building such as when articulating upper and lower dental casts or filling a void. There is commercially available, gypsum that is packaged in small unit size foil bags. This supply method reduces to some degree the dust associated with transferring the dry powder from a bulk container to a gypsum bin.

This small unit packaging still produces dust to the immediate breathing hazard of the worker when it is emptied into a mixing bowl for preparation of the mix with liquid and has not eliminated the problems of washing utensils and clogging of the sinks, or the dusting off of the surface of the set gypsum.

U.S. Pat. Nos. 4,299,790, 3,958,997 and 3,989,220 disclose a shaker-mixer-molding assembly and a gypsum composition. These methods and compositions do not address or reduce the dusting problem associated with measuring, weighing and transferring a dry gypsum powder from a bulk packaging container or from a bulk storage container to a mixing vessel. Neither do they eliminate the need to wash the mixing vessel, measuring devices and mix utensils in preparation for the next mix. They are related to a performance composition and a speedy method of direct filling a specific mold that is attached by design to the mixing vessel, an object of which is a molding apparatus which is a principle part of the shaker-mixer assembly for matched attachment and pouring.

Similar to the shaker-mixer-mold device of U.S. Pat. Nos. 3,958,997 and 3,989,220 but without the attached mold, there is commercially available a pre-loaded syringe, containing an alginate composition dry powder encapsulated within the lower portion of the syringe. In the upper portion of the syringe and separated by a thin membrane is encapsulated a pre-measured amount of liquid. To make a dental impression mold the pre-loaded dual compartmented syringe is first fitted to a mechanical device that punctures the internal membrane allowing the powder and liquid to combine. The syringe is secondarily placed into a separate electro-mechanical shaker device that vigorously shakes the syringe for a specified time. The syringe is thirdly placed into a separate mechanical plunger device that is used to force the mixed material into an impression tray for the molding process. With this device the pre-measured amounts of both the powder and the liquid are sealed in a single unalterable container device and the volumes are determined and controlled by the manufacturer.

This denies the gypsum worker the required freedom to alter the liquid/powder ratio to obtain molds or castings of variable physical properties or to add a filler, additive or aggregate to the powder as is sometimes desirable or necessary. Additionally, as a practical matter this apparatus with its internal membrane to separate powder and liquid requires specialized filling, loading and assembly machinery by the manufacturer.

Together with all of the required mechanical and electro-mechanical devices necessary for its proper function, it is costly, time consuming and impractical to the large scale production of volume gypsum castings or alginate impression molds.

Similar to the commercially available pre-loaded syringe, U.S. Pat. No. 5,743,431 discloses a fluid dispenser and activator adaptor. This device primarily provides for dispensing of fluid pastes cements, chalking compounds, resins, lubricants and silicone type impression materials. Mixing of two part dry powder and water materials are not discussed.

Attempts to strengthen and harden gypsum appear to have focused on the overall strength and hardness verses the surface durability and/or improving the surface texture.

U.S. Pat. No. 5,026,428 discloses an aqueous solution of boric oxide that is converted to boric acid in water and silicic acid. This solution is mixed with gypsum to increase the overall hardness and decrease the setting time.

U.S. Pat. No. 4,148,660 discloses a gypsum composition that contains perlite and non-fibrous fillers such as silica and mica.

U.S. Pat. No. 4,268,310 discloses a gypsum composition containing formaldehyde a hydrocarbon and magnesium aluminum silicate.

Several U.S. Patents discuss and disclose the use of gypsum/Portland cement combination products with improved hardening or accelerated set properties, or with unique, industry specific, desirable properties. For example U.S. Pat. No. 5,560,774 discloses a method for accelerating the setting time and hardening of hydraulic binders and eliminating the worker and machinery hazards of traditional accelerators by the addition of calcium aluminate, calcium sulfoaluminate and aluminum sulfate. U.S. Pat. No. 4,196,008 uses Carboxy methyl cellulose to maintain strength while rendering the slurry pumpable. U.S. Pat. No. 4,762,561 strengthens basic concrete by reducing the normal levels of iron oxides in the mix.

A consequence of adding chemical adulterants to gypsum is the undesirable effect that such additives have on the dimensional integrity of the set casting. The result is usually a casting with excessive expansion and reduced accuracy. In some instances accuracy is not important as for example with small figurines. In other castings such as for dental, and foundry castings or molds, accuracy and expansion are very critical.

Chemical additives may also adversely effect the set time of gypsums thereby extending work projects. The use therefore of any chemical additive for the improvement of one aspect of a gypsum casting should be carefully selected or formulated to maintain the desirable qualities of no delayed setting time and reliable dimensional accuracy.

U.S. Pat. No. 3,407,924 teaches using a unit-size container for a vacuum treated gypsum that is to be used as a mixing vessel to provide the dental casting composition. This container for some reason is not widely used in the dental industry. This is most likely due to the extra step of vacuum treating the gypsum. This patent does not suggest nor teach the advantageous use of the dental casting compositions of the present convention.

Therefore while the aforementioned traditional methods and patents disclose a variety of devices and methods for producing gypsum castings, and accomplish to a degree their intended objectives, the gypsum dust and handling problems continues to present problems.

Accordingly, it is an object of the present invention to provide a multi-part aqueous gypsum dental casting composition that has a first gypsum composition and a second water composition. The casting composition has either or both a compound and an acid. The compound is selected from ammonium chloride, potassium chloride, ammonium fluorosilicate, magnesium fluorosilicate, magnesium sulfate, magnesium aluminum sulfate, aluminum sulfate, aluminum ammonium sulfate, and non-reactive mixtures thereof. The compound is in either or both of the first and second composition. The acid is selected from oxalic acid, boric acid, phosphoric acid, citric acid, sodium citric acid, trisodium citric acid, tartaric acid, sulfuric acid, acetic acid, formic acid, malic acid, ascorbic acid, aspartic acid and mixtures thereof. The acid is in either or both of the first and second composition. When the casting composition is free of the compound, there are at least two of the acids. The first and second compositions are maintained separately and mixed when the casting is to be prepared.

A still further object of the present invention is to provide the dosage size gypsum dental casting shaped container wherein, the shaped container contains 50 to 600 gms of gypsum and contains per 100 parts by weight of gypsum (a)

0.2 to 12 parts by weight of at least one compound selected from ammonium chloride, potassium chloride, ammonium fluorosilicate, magnesium fluorosilicate, magnesium sulfate, magnesium aluminum sulfate, aluminum sulfate, aluminum ammonium sulfite, and non-reactive mixtures thereof, and 0.2 to 18 parts by weight of at least one acid selected from oxalic acid, boric acid, tri-sodium citric acid and phosphoric acid or (b) 0.2 to 24 parts by weight of at least two of the acids.

A still further object of the present invention is to provide a multi-part gypsum casting system which a first gypsum part and a second water part, the total content of the system being for every 100 parts by weight of gypsum, there are 20 to 40 parts by weight of water, and (a) 0.2 to 12 parts by weight of at least one compound selected from ammonium chloride, potassium chloride, ammonium fluorosilicate, magnesium fluorosilicate, magnesium sulfate, magnesium aluminum sulfite, aluminum sulfate, aluminum ammonium sulfate, and non-reactive mixtures thereof; and 0.2 to 18 parts by weight of at least one acid selected from the following acids: oxalic acid, boric acid, phosphoric acid, citric acid, sodium citric acid, tri-sodium citric acid, tartaric acid, sulfuric acid, acetic acid, formic acid, malic acid, ascorbic acid and, aspartic acid, or (b) the compound and/or acid being mixed with either or both of the gypsum or water.

SUMMARY OF THE INVENTION

The multi-part dental casting composition has at least two separate parts. The first part is a dry gypsum powder such as Hydrocal (U.S. Gypsum Corp.) and the second part is water. Mixed with the gypsum and/or dissolved in the water is 0.2 to 12 parts by weight of at least one compound selected from ammonium chloride ($NH_4Cl$), potassium chloride (KCl), ammonium fluorosilicate [$(NH_4)_2SiF_6$], magnesium fluorosilicate ($MgSiF_6$), aluminum ammonium sulfate [$AlNH_4(SO_4)_2$], magnesium sulfate ($MgSO_4$), aluminum sulfate $AL_2(SO_4)_3$, and non-reactive mixtures thereof. Also it is preferred that there is also mixed with gypsum and/or water 0.2 to 18 parts by weight of at least one acid selected from the following acids: oxalic acid, boric acid, phosphoric acid, citric acid, sodium citric acid, tri-sodium citric acid, tartaric acid, sulfuric acid, acetic acid, formic acid, malic acid, ascorbic acid, aspartic acid, and mixtures thereof. When the casting composition does not contain one of the compounds, then there are at least two of the acids mixed with either or both of the gypsum and water. When only an acid is used, the preferred range is 0.2 to 24 parts by weight of the two acids but this may be as high as 0.2 to 36 parts by weight of the two acids depending on which acid is selected.

The preferred multi-part dental casting composition uses both the acid and compound and has the compound and acid dissolved in the water. The dry gypsum powder is pre-packaged in dosage sized containers by a manufacturer or distributor. The dosage containers are hereinafter defined as "shaped containers" that are ridged or semi-ridged, plastic, rubber-like, paper or coated paper disposable containers that generally hold their shape and simulate in form and function a standard gypsum mixing bowl. The preferred shape of the container is a curved side wall to allow complete mixing and a flat bottom to allow easy storage. The dry gypsum powder occupies approximately only ½ to ¾ of the available volume of the container. The shaped container does not include a plastic freezer bag type container as is shown in U.S. Pat. No. 5,709,467.

The shaped containers may be any one of a variety of sizes but for illustrative purposes, generally resembling the packaging of common individual serving, lunch deserts such as pudding or yogurt with a package cover that is sealed and removable, or a half pint milk carton. This unit packaging of the dry gypsum powder component allows the gypsum to be mixed within the unit package container. The unit package may have a resealable cover and/or lid. The water component with any or all of the above compounds and acids dissolved therein is also preferably pre-loaded into unit dosage packages wherein the unit dose of the liquid is matched to the unit quantity of the dry powder such that the liquid/powder ratio is as recommended by the manufacturer. Generally more liquid than necessary is preloaded so that the liquid to powder ratio may be adjusted according to the preference of the user (dentist). Alternatively the liquid may be provided in a bulk container and a re-fillable and re-useable package such as a syringe is provided so that the user may adjust the liquid/powder ratio more conveniently according to the desired physical properties of the casting.

When a re-sealable container is used, the cover is removed or pierced with a syringe needle to mix the water component with the gypsum. Then the container is re-sealed and the gypsum and water mixture are vigorously mixed by being vigorously shaken by the user or by a mechanical shaker similar to those used to mix paint. Thereafter, the cover is removed and the gypsum slurry may be poured into or packed onto any intended mold or configuration directly from the unit package that has also served as the mixing vessel.

The resulting gypsum dental casting displays no delayed setting time, decreased setting expansion and it has a smooth, silky and glossy, durable surface.

The general configuration of the container is such that it can preferably be used as a mixing bowl that allows easy mixing with a spatula. This being the configuration that a dentist is used to. The container permits the in-situ preparation of the gypsum casting composition and is only partially full with dry gypsum powder so as to be suitable for receiving the liquid component and serving as the spatula mixing vessel.

In one embodiment, for the water component, a larger than unit dose syringe is provided as an easy delivery system for the water component. There are innumerable package configurations that may satisfy the spirit and scope of the invention to including packaging configurations for the liquid component, squeezable or depressible bottles with or without needle like plastic or metal dispensing tips, or combination devices that comprise a single container that includes a container for the dry powder that is suitable for serving as a bowl-like mixing vessel and a volume adjustable liquid container/dispenser or an attached liquid filled pouch.

The above system of multi-containers for the gypsum, compounds and/or acids, and water drastically eliminates the risk of releasing dried gypsum powder into the immediate airspace. Additionally, disposable unit containers provides the convenience of not needing to clean the gypsum powdered bowls, sink area, and not clogging the sink drains. The compounds and acids may be conveniently packaged in separate disposable containers if desired and mixed with the water when they are to be used.

The above, as well as other objects and advantages of the present invention, will become more apparent from the following description of the preferred embodiments and reference being made to the accompanying drawings.

FIG. 1 is a perspective view of an individual unit of dry powder gypsum packaged in the mixing vessel/package of the preferred embodiment.

FIG. 2 is a perspective view of a unit dose syringe containing the liquid component of the composition of the preferred embodiment.

FIG. 3 is a perspective partial cross-sectional view of adding the liquid component of FIG. 2 to the dry powder gypsum package of FIG. 1.

FIG. 4 is a perspective view of the syringe of FIG. 2 being filled with the liquid component of my invention from a bulk container.

Figure 5:
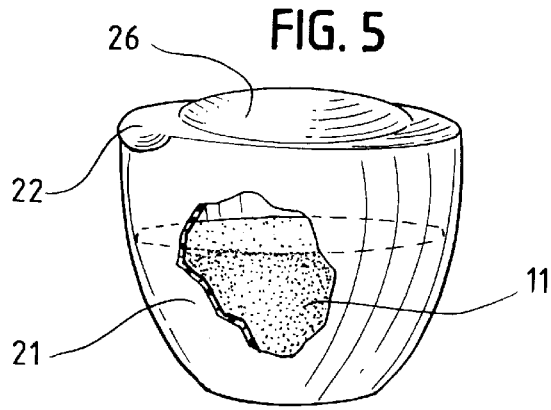
FIG. 5 is a perspective view of dry powder gypsum of my invention having multi-container component and a liquid component.

Generally the invention provides a composition and packaging system for producing unit dose gypsum dental castings. The containers are a ridged or semi-ridged container that is pre-filled with a gypsum composition. There is a second container that has a water component. The selected compounds and/or acids are mixed with either or both of the gypsum or water. When a casting is to be prepared, the water component is mixed in the disposable gypsum container and used for a dental casting. Then the used container is discarded.

The compound is selected from ammonium chloride, potassium chloride, ammonium fluorosilicate, magnesium fluorosilicate, magnesium sulfate, magnesium aluminum sulfate, aluminum sulfate, aluminum ammonium sulfate, and non-reactive mixtures thereof. The acid is selected from oxalic acid, boric acid, phosphoric acid, citric acid, sodium citric acid, tri-sodium citric acid, tartaric acid, sulfuric acid, acetic acid, formic acid, malic acid, ascorbic acid, aspartic acid, and mixtures thereof.

My preferred invention provides that for every 100 parts by weight of gypsum, there should be 20 to 40 parts by weight of water and an effective amount of the compound and/or acid. The effective total amount for each 100 parts by weight of gypsum is, (a) 0.2 to 12 parts by weight of the compound; and (b) 0.2 to 24 parts by weight of at least two acids.

Referring to FIG. 1 a rigid plastic bowl-type container 10 is filled with 100 to 600 gm of a dry gypsum dental powder 11 to approximately three quarters of its normal capacity. The shape of the container 10 is generally similar to the shape of a standard plaster mixing bowl wherein the sides are curved and the bottom is flat. The size of the container is such that it can comfortably contain for mixing not only the gypsum, but also the required amount of liquid needed to form the casting composition and still leave room for mixing. Although not shown, the container could be a milk carton type container.

The container is designed to be disposable following a single use. The container 10 is sealed and covered with a peel off type package seal 12 as also would be commonly used in the food packaging industry. The container could also have a removable lid (not shown). Such a lid would give extra protection to the peel off seal 12.

Referring to FIG. 2, there is shown a disposable type plastic syringe 13 which contains the water component 14 of the casting composition. The size of the syringe would be commensurate with the container 10 it is to be packaged with. The syringe is sized to hold preferably, approximately 25% greater amount of liquid than would be necessary for the casting composition. This allows the user (the dentist to adjust the consistency of the casting composition. The syringe preferably has volume graduation markings and has an appropriate removable needle 16. Alternatively, the water component may be provided in a bulk container 18 (FIG. 4) and an empty refillable and re-usable syringe 19 (FIG. 4) or any other desirable container is provided so the user may adjust the liquid/powder ratio more conveniently according to the desired physical properties of the casting.

Figure 6:
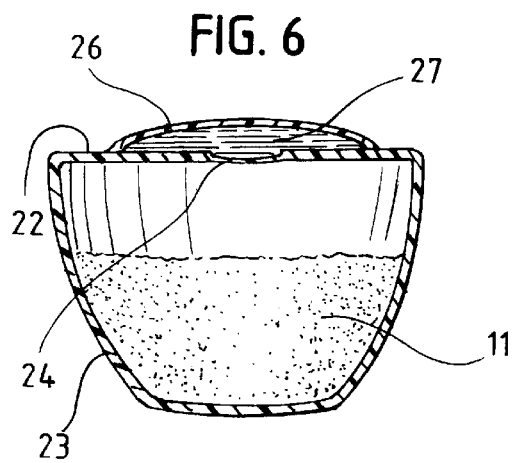
FIG. 6 is a cross sectional view of the multi compartment container of FIG. 5.
Figure 7:
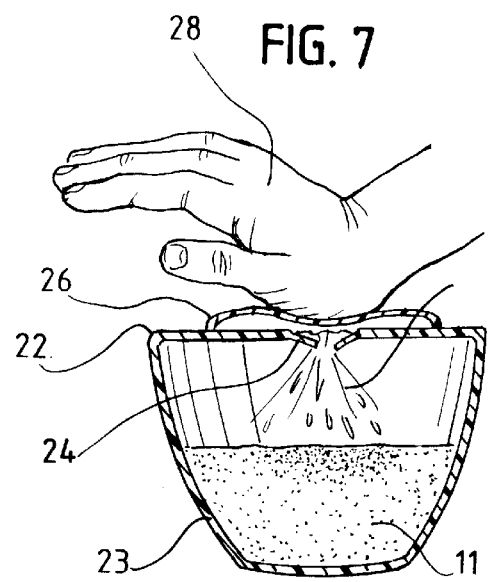
FIG. 7 is the cross sectional view of FIG. 6 showing the use of the multi-compartment container of FIG. 5.

Referring to FIGS. 5–7, there is shown an alternative two-part ridged container 21 containing a dry gypsum powder 11. The container 21 has a container seal 22 to provide a segregated gypsum compartment 23. The seal 22 is manufactured with a weakened center portion 24 and has as a part thereof, a laminated pouch or second water compartment 26 on its top side that contains a recommended, matched amount of the water component 27. This weakened center portion 24 is designed to rupture at a pre-determined pressure. The laminated pouch 26 is similar to standard individual unit size servings of condiments, such as mustard, ketchup, relish, etc. except its bottom wall is also the seal 22. The filling and lamination process is well within capabilities of commonly available packaging methods in the food and beverage industry.

Referring now to FIG. 7, when the worker desires to make a gypsum casting the worker places his hand 28 firmly on the laminated sealed pouch 26 and applies pressure until the weakened center portion 24 of the package seal 22 ruptures and the water component 27, is released into compartment 23 to combine with the dry gypsum component 11. Mixing is then accomplished either by shaking vigorously or by peeling off the package seal 22 with the attached empty pouch 26 and mixing with a conventional spatula.

Figure 8:
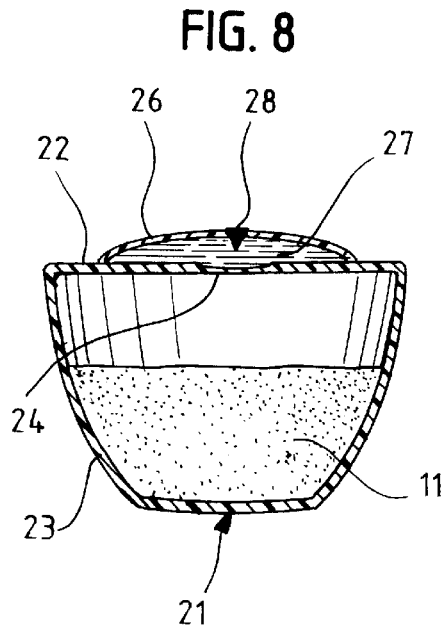
FIG. 8 is a cross sectional view of another multi-compartment container according to the present invention.
Figure 9:
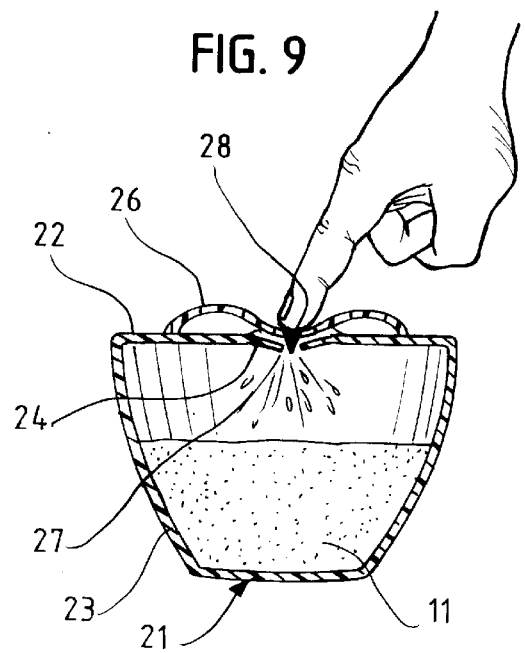
FIG. 9 is the cross sectional view of FIG. 8 showing the use of the multi-compartment container of FIG. 8.

FIGS. 8 & 9 represent the same ridged plastic unit size multi compartment container 21 of FIG. 7 except the laminated liquid filled pouch 26 with an alternative puncture device 28 as a part thereof. The puncture component 28 aids in rupturing the weakened center portion 24. As shown in FIG. 9, Finger pressure is applied to an external portion of the puncture device 28 causes the puncture device 28 to penetrate the weakened center portion 24 to release liquid 27 into the container compartment 23. Mixing is then accomplished either by shaking vigorously or by peeling off the package seal 22 with the attached empty pouch 26 and mixing with a conventional spatula.

To make the preferred water component, per 100 gm of gypsum, there are 0.2 to 12 gm of the compound and 0.2 to 18 gm of the acid composition is dissolved in 20 to 40 gm or 20 ml to 40 ml of water. The acid is in dry form, i.e., sulfuric and the phosphoric acids are the crystalline forms of the acid.

As is shown in FIGS. 1–3, to make the dental casting, the needle portion 16 of the syringe 13, is used to puncture the package seal 12 of the container 10 and the plunger of the syringe is depressed thereby injecting the water component 14 into the still sealed container. The syringe is removed and discarded if no additional water component is needed. The container 10 is then held in one hand with an index finger covering the syringe needle entry hole and shaken vigorously for 10–15 seconds. The container may alternately or even additionally be placed in contact with a vibrator for 10–15 seconds to assist in the wet out. The needle entry hole being sealed by a piece of adhesive tape. Alternatively, a removable lid may be placed on the container over the seal punctured gel 12 and then the container shaken.

Immediately thereafter, the lid, if there is one, is removed and the package seal is peeled off and discarded and the mixed gypsum is poured into a mold or additionally mixed with a spatula. If the consistency of the gypsum casting composition is such that it is not readily pourable, the mixed gypsum is scooped out with a spatula for placement into or onto a mold for shaping. Following the filling of the mold, the container is discarded. The resultant casting is without delayed setting, with good accuracy and displays an uncommonly smooth, silky, glossy and durable surface with no gypsum powder residue.

In those cases where the worker desires to adjust the liquid powder ratio, the amount of liquid injected into the container may be more or less according to the desired physical properties of the mix or the desired physical properties of the casting and controlled by the depression of the plunger in relation to the graduation markings on the syringe body.

In those cases when the worker desires to add a filler, an aggregate or additional powder to the mix, it is easily accomplished by removing the package seal prior to injecting the liquid component, adding the material of choice, secondarily injecting the desired amount of liquid into the open container, and completing the mixing with a standard spatula or replacing the seal and/or lid and shaking the container.

In those cases when a user desires to alter the setting time of the gypsum mix as is frequently desirable, a higher amount of an acceleration component such as aluminum ammonium sulfate can be added to the water and/or gypsum component. The precise amount below the point of saturation is dependent upon the degree of acceleration desired. A secondary method of accelerating the set time of the castings is by raising the temperature of the liquid thereby speeding up the initiation of the gypsum-water reaction.

My preferred dental casting composition uses per 100 gm of gypsum, 0.2 to 12 gm of aluminum ammonium sulfate, and 0.2 to 12 gm boric acid, and 0.2 to 12 gm of phosphoric or tri-sodium citric acid, all dissolved in (20 to 40 ml) 20 gm to 40 gm of water.

The following examples 2–100 of the present invention are for illustrative purposes only and are not intended to limit the scope of the present invention. Example 1 illustrates the known manner of preparing gypsum dental castings. Examples 2 and 3 shows that the use of only one acid does not provide an acceptable gypsum dental casting.

EXAMPLE 1

30 milliliters (30 grams) of room temperature (68–72° F.) water was mixed with 100 grams of room temperature gypsum dental casting material—Hydrocal. The aqueous mixture was mixed for approximately one minute with a spatula to produce a gypsum casting mixture having a paste/slurry consistency. The wet standard gypsum mixture was poured into a test dental mold. The gypsum casting was removed from the test mold. The setting time was 30 minutes; the casting increased 0.20% in size from that poured. The surface of the casting had a dry, chalky, gypsum powder residue thereon.

EXAMPLE 2

A water solution was prepared by dissolving approximately 2 gm of phosphoric acid was added to and dissolved into 30 gm. of water. A plastic container being sealed with a removable cover was about half fall with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting displayed a retarded setting time. The setting time was 3 hours. The surface was dry and chalky.

EXAMPLE 3

A water solution was prepared by dissolving approximately 2 gm of boric acid in gm(30 ml) of water. A plastic container being sealed with a removable cover was about half fall with 100 gm of the Hydrocal gypsum. The cover was removed and the water-boric acid solution was poured into the container and mixed with a spatula for about 1 minute to prepare a dental casting mixture.

The dental casting mixture was poured into a dental test mold. The resulting gypsum casting displayed a dry, chalky surface similar to the castings that were prepared according to above Examples 1. The setting time for the casting utilizing only boric acid was 2 hours.

EXAMPLE 4

A water solution was prepared by dissolving approximately 2 gm of aluminum ammonium sulfate and 2 gm of boric acid, and 1 gm of phosphoric acid in 30 gm of water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting displayed no delayed setting, increased expansion and had an improved silky and glossy surface verses the castings that were prepared according to above Examples 1. The setting time was 15 minutes; the casting increased 0.10% in size from that poured. The surface of the casting had no powder residue.

EXAMPLE 5

A water solution was prepared by dissolving approximately 2 gm of ammonium chloride and 2 gm of boric acid, and 1 gm of phosphoric acid in 30 gm of water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Examples 1. The setting time was 30 minutes; the casting increased 0.10% in size from that poured. The surface of the casting had no powder residue.

EXAMPLE 6

A water solution was prepared by dissolving approximately 2 gm of ammonium fluorosilicate and 2 gm of boric acid, and 0.5 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 30 minutes; the casting increased 0.10% in size from that poured. The surface of the casting had no powder residue.

EXAMPLE 7

A water solution was prepared by dissolving approximately 1 gm of magnesium fluorosilicate and 2 gm of boric acid, and 00.05 gm phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 20 minutes; the casting increased 0.10% in size from that poured. The surface of the casting had no powder residue.

EXAMPLE 8

A water solution was prepared by dissolving approximately 2 gm of aluminum sulfate and 2 gm of boric acid, and 1 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 15 minutes; the casting increased 0.10% in size from that poured. The surface of the casting had no powder residue.

EXAMPLE 9

A water solution was prepared by dissolving approximately 2 gm of magnesium sulfate and 2 gm of boric acid, and 1 gm phosphoric acid in 30 ml water. A plastic container being sealed with a removable cover was about half fill with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 15 minutes; the casting increased 0.10% in size from that poured. The surface of the casting had no powder residue.

EXAMPLE 10

A water solution was prepared by dissolving approximately 2 gm of aluminum sulfate and 1 gm of magnesium sulfate and 2 gm of boric acid, and 1 gm of tri-sodium citric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 15 minutes; the casting increased 0.10% in size from that poured. The surface of the casting had no powder residue.

EXAMPLE 11

A water solution was prepared by dissolving approximately 2 gm of potassium chloride and 2 gm of boric acid, and 1 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 30 minutes; the casting increased 0.10% in size from that poured. The surface of the casting had no powder residue.

EXAMPLE 12

A water solution was prepared by dissolving approximately 2 gm of oxalic acid and 1 gm of boric acid, and 0.5 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 20 minutes; the casting increased 0.10% in size from that poured. The surface of the casting had no powder residue.

EXAMPLE 13

A water solution was prepared by dissolving approximately 1 gm of aluminum ammonium sulfate and 0.5 gm of oxalic acid and 1.5 gm of boric acid, and 1 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture.

The mixture was poured into a dental test mold. The resulting gypsum dental casting had an improved silky and glossy surface verses the castings that were prepared according to above Example 1. The setting time was 20 minutes; the casting increased 0.10% in size from that poured. The surface of the casting had no powder residue.

EXAMPLE 14

A water solution was prepared by dissolving approximately 2 gm of aluminum ammonium sulfate and 2 gm of magnesium sulfate and 3 gm of boric acid, and 0.5 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold.

The resulting gypsum dental casting had an improved silky and glossy surface verses the castings that were prepared according to above Example 1. The setting time was 10 minutes; the casting increased 0.10% in size from that poured. The surface of the casting had no powder residue.

EXAMPLE 15

A water solution was prepared by dissolving approximately 1.5 gm of aluminum ammonium sulfate and 1 gm of ammonium chloride and 00.05 gm of oxalic acid, and 2 gm of boric acid, and 1 gm of phosphoric acid in 30 ml water. A plastic container being sealed with a removable cover was about half full with 100 gm of the Hydrocal gypsum. The cover was a removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 20 minutes; the casting increased 0.10% in size from that poured. The surface of the casting had no powder residue.

EXAMPLE 16

A water solution was prepared by dissolving approximately 2 gm of aluminum ammonium sulfate and 1 gm of potassium chloride and 1.5 gm of boric acid, and 1 gm of tri-sodium citric and 00.05 gm of phosphoric acid in 30 ml water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Examples 1 and 2. The setting time was 20 minutes; the casting increased 0.10% in size from that poured. The surface of the casting had no powder residue.

EXAMPLE 16A

A water solution was prepared by dissolving approximately 0.5 gm of aluminum ammonium sulfate was dissolved in 30 gm of water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting had an improved silky and glossy surface verses the castings that were prepared according to above Example 1. The setting time was 4 minutes; the casting increased 0.10% in size from that poured. The surface of the casting had no powder residue.

EXAMPLE 16B

A water solution was prepared by dissolving approximately 2 gm of aluminum ammonium sulfate and 2 gm of boric acid, and 1.5 gm of tri-sodium citric acid in 30 gm of water. A plastic container being sealed with a removable cover was about half full with 100 gm of the Hydrocal gypsum. The cover was removed and the water solution was poured into the container and mixed with a spatula for about 1 minute to prepare a dental casting mixture. The mixture was poured into a dental test mold. The resulting gypsum dental casting displayed no delayed setting nor increased expansion and had an improved silky and glossy surface verses the castings that were prepared according to above Example 1. The setting time was 20 minutes; the casting increased 0.10% in size from that poured. The surface of the casting had no powder residue.

In the following Examples 17–100, all of the amounts are set forth in grams (gm). In all of the examples 100 gms. of gypsum was used and this was placed in a rigid plastic container having a removable lid. Prior to closing the container, any non-water components which were to be added to the gypsum were added and mixed therewith by adding them, closing the container and shaking the container for 10–30 seconds. The container contents were at room temperature.

The water component was in a separate container and had 30 gm (30 ml) of water and dissolved in the water were the amounts of compound and/or acid as noted in the following Examples. This water component was at room temperature. The gypsum container lid was taken off and the water component was poured into the gypsum container. The gypsum container was then reclosed and shaken vigorously by hand for 10 to 30 seconds. The container was opened again and the resulting dental casting composition was poured into test molds. The resulting gypsum castings had improved silky and glossy surfaces with no powder residue.

In Examples 17 to 35 the acids are dissolved in the water. In Examples 36–45, the acid is dissolved in the water and the compounds are mixed with the gypsum. In Examples 46–72, the compounds are dissolved in water and the acids are mixed with the gypsum. In Examples 73–100, the compounds and acids are dissolved in the water.

| Example | 17 | 18 | 19 | 20 | 21 | 22 | 23 | 24 | 25 | 26 | 27 | 28 | 29 | 30 | 31 | 32 |
|---|---|---|---|---|---|---|---|---|---|---|---|---|---|---|---|---|
| ACID COMPOUNDS | | | | | | | | | | | | | | | | |
| Boric | 1 | 0.5 | 2 | 1 | 2 | 1 | 1 | 1 | 1 | 1 | 1 | | | | | |
| Phosphoric | 1 | 0.5 | | 0.5 | | | | | | | | 1 | 0.5 | 0.25 | 0.25 | 1 |
| Citric | | | | 0.5 | | | | | | | | 0.5 | | | | |
| Na Citric | | | | | | | | | | 0.5 | | | 0.5 | | | |
| Na$_3$ Citric | | | | | 0.5 | | | | | | | | | 0.5 | | |
| Tartaric | | | | | | 0.5 | | | | | | | | | 0.5 | |
| Sulfuric | | | | | | | 0.5 | | | | | | | | | 0.5 |
| Oxalic | 1 | 0.5 | 1 | 0.5 | 0.5 | 0.5 | 0.5 | 0.5 | 0.5 | 1 | 0.25 | 1 | 0.25 | 0.25 | 0.25 | 1 |
| Acetic | | | | | | | | 0.5 | | | | | | | | |
| Formic | | | | | | | | | | | 0.5 | | | | | |
| Ascorbic | | | | | | | | | | | | | | 0.5 | | |

-continued

| | | | | | | | | | | | | | | | | |
|---|---|---|---|---|---|---|---|---|---|---|---|---|---|---|---|---|
| Malic | | | | | | | | | | | 0.5 | | | | | |
| Aspartic | | | | | | | | | | | | | | | | 0.5 |
| COMPOUNDS | | | | | | | | | | | | | | | | |
| NH₄Cl | | | | | | | | | | | | | | | | |
| KCl | | | | | | | | | | | | | | | | |
| (NH₄)₂SiF₆ | | | | | | | | | | | | | | | | |
| MgSiF₆ | | | | | | | | | | | | | | | | |
| AlNH₄(SO₄)₂ | | | | | | | | | | | | | | | | |
| MgSO₄ | | | | | | | | | | | | | | | | |
| Al₂(SO₄)₃ | | | | | | | | | | | | | | | | |
| Set Time (Min) | 30 | 30 | 30 | 30 | 30 | 30 | 30 | 30 | 30 | 30 | 30 | 30 | 30 | 30 | 30 | 30 |
| % Increased | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 |

| Example | 33 | 34 | 35 | 36 | 37 | 38 | 39 | 40 | 41 | 42 | 43 | 44 | 45 | 46 | 47 | 48 |
|---|---|---|---|---|---|---|---|---|---|---|---|---|---|---|---|---|
| ACID COMPOUNDS | | | | | | | | | | | | | | | | |
| Boric | | | | 1 | 2 | 2 | 1 | 1 | | | | | | 2 | 2 | 2 | 2 |
| Phosphoric | 1 | 1 | | 1 | | | 0.5 | | 1 | 1 | 1 | 1 | | | | | |
| Citric | | | | | | | | | | 1 | | | | 1 | | 1 | 0.5 |
| Na Citric | | | | | | | | 1 | | | | | | | | | |
| Na₃ Citric | | | | | | | 1 | | | | | | | | | | |
| Tartaric | | | | | | 1 | | | | | | | | | | | |
| Sulfuric | | | | | | | | | | | | | 0.05 | | | | |
| Oxalic | | | 2 | | | | | | | | | | | | | | |
| Acetic | 0.5 | | | | | | | | | | | | | | | | |
| Formic | | 0.5 | | | | | | | | | | | | | | | |
| Ascorbic | | | | | 1 | | | | | | | | | | | | |
| Malic | | | 0.5 | | | | | | | | | | | | | | |
| Aspartic | | | 0.5 | | | | | | | | | | | | | | |
| COMPOUNDS | | | | | | | | | | | | | | | | |
| NH₄Cl | 1 | | | 1 | | | | | | | | | | 1 | | | |
| KCl | | 1 | | 1 | | | | | | | | | | | 1 | | |
| (NH₄)₂SiF₆ | | | | | | | 2 | | | | | | | | | 1 | |
| MgSiF₆ | | | | | | 1 | | | | | | | | | | | 0.5 |
| AlNH₄(SO₄)₂ | 0.5 | 1 | | | | | | 1 | | | | 1 | 1 | 2 | | | |
| MgSO₄ | | | | | 2 | | | | | 2 | | | | | | | |
| Al₂(SO₄)₃ | | | 1 | | 1 | | | | | | 1 | | | | | | |
| Set Time (Min) | 15 | 15 | 15 | 15 | 15 | 15 | 15 | 15 | 15 | 15 | 15 | 15 | 15 | 15 | 15 | 15 |
| % Decrease | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |

| Example | 49 | 50 | 51 | 52 | 53 | 54 | 55 | 56 | 57 | 58 | 59 | 60 | 61 | 62 | 63 | 64 |
|---|---|---|---|---|---|---|---|---|---|---|---|---|---|---|---|---|
| ACID COMPOUNDS | | | | | | | | | | | | | | | | |
| Boric | 2 | 2 | 2 | 2 | 2 | 2 | | | 0.5 | | | | | | | |
| Phosphoric | | | | | | | 1 | 0.5 | 1 | 1 | 0.25 | 0.25 | 1 | 0.25 | 0.5 | 0.25 |
| Citric | | | | | | | 0.5 | 0.5 | 0.25 | | | | | | | |
| Na Citric | | | | | | | | | | | | | | | | |
| Na₃ Citric | | | | | | | | | | | | | | | | |
| Tartaric | 1 | 0.5 | | | | | | | | 0.25 | 1 | | | | | |
| Sulfuric | | | 0.25 | | | | | | | | | 0.25 | | | | |
| Oxalic | | | | | | | | | | | | | 2 | | | |
| Acetic | | | | | | | | | | | | | | 1 | 1 | |
| Formic | | | | | 1 | | | | | | | | | | | |
| Ascorbic | | | | | | | | | | | | | | | | 1 |
| Malic | | | | | | 0.5 | | | | | | | | | | 0.25 |
| Aspartic | | | | | | 0.5 | | | | | | | | | | |
| COMPOUNDS | | | | | | | | | | | | | | | | |
| NH₄Cl | | | | | | | 0.5 | | | 1 | | | | | | |
| KCl | | | | | 2 | | | | | | | 1 | | 2 | | |
| (NH₄)₂SiF₆ | | | | | | | | | | | | | | | | |
| MgSiF₆ | 1 | | | | | | | 1 | | | | | | | | |
| AlNH₄(SO₄)₂ | | | | 2 | | | | | 2 | | 2 | | | | 2 | 2 |
| MgSO₄ | | 2 | | | | | | | | | | | | | | |
| Al₂(SO₄)₃ | | | 2 | | | | | | | | | | | | | |
| Set Time (Min) | 15 | 15 | 15 | 15 | 15 | 15 | 15 | 15 | 15 | 15 | 15 | 15 | 15 | 15 | 15 | 15 |
| % Decrease | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 | 0.15 |

| Example | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|
| ACID COMPOUNDS | | | | | | | | | | | | | | | | |
| Boric | | | | | | | | | | | | | | | | |
| Phosphoric | | | | | | | | | | | | | | | | |
| Citric | | | | | | | | | | | | | | | | |

-continued

| | | | | | | | | | | | | | | | | |
|---|---|---|---|---|---|---|---|---|---|---|---|---|---|---|---|---|
| Na Citric | | | | | | | | | | | | | | | | |
| $Na_3$ Citric | 1 | 1 | 1 | 1 | 1 | 1 | 1 | 1 | | | | | | | | |
| Tartaric | | | 0.25 | 0.25 | | | | | | | | | | | | |
| Sulfuric | | | | | | | | | | | | | | | | |
| Oxalic | | | | | | | | | | | | | | | | |
| Acetic | | | | | | | 1.5 | 0.05 | | | | | 1 | 1 | | |
| Formic | | | | | | | | | | 1 | 1.5 | | | | | |
| Ascorbic | | | | | | | | | | | | | | | | |
| Malic | | | | | | | | | | | | | | | | |
| Aspartic | | | | | | | | | | | | | | | 0.5 | 0.5 |
| COMPOUNDS | | | | | | | | | | | | | | | | |
| $NH_4Cl$ | | | 2 | | | | | | 1.5 | | | | | | | |
| KCl | | | | | 1.5 | | | | | | | | | | | |
| $(NH_4)_2SiF_6$ | | 1.5 | | | | | | | | 3 | | | | | | |
| $MgSiF_6$ | | | | | | 1.5 | | | | | | | | 3 | | |
| $AlNH_4(SO_4)_2$ | 1.5 | | | | | | | | | | | 1.5 | 1.5 | | 1.5 | 1.5 |
| $MgSO_4$ | | | | | | | 3 | | | | 2.5 | | | | | |
| $Al_2(SO_4)_3$ | | | | 1.5 | | | | 0.5 | | | | | | | | |
| Set Time (Min) | 15 | 15 | 15 | 15 | 15 | 15 | 15 | 15 | 15 | 15 | 15 | 15 | 15 | 15 | 15 | 15 |
| % Increased | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |

| Example | 81 | 82 | 83 | 84 | 85 | 86 | 87 | 88 | 89 | 90 | 91 | 92 | 93 | 94 | 95 | 96 |
|---|---|---|---|---|---|---|---|---|---|---|---|---|---|---|---|---|
| ACID COMPOUNDS | | | | | | | | | | | | | | | | |
| Boric | | | | | | | | | | | | | | | | |
| Phosphoric | | | | | | | | | | | | | | | | |
| Citric | | | | | | | | | | | | | | | | |
| Na Citric | | | | | | | | | | | | | | | | |
| $Na_3$ Citric | | | | | | | | | | | | | | | | |
| Tartaric | | | | | | | | | | | | | | | | |
| Sulfuric | | | | | | | | | | | | | | | | |
| Oxalic | | | | | | | | | | | | | | | | |
| Acetic | | | | | | | | | | | | | | | | |
| Formic | | | | | | | | | | | | | | | | |
| Ascorbic | | | | | | | | | | | | | | | | |
| Malic | | | | | | | | | | | | | | | | |
| Aspartic | | | | | | | | | | | | | | | | |
| COMPOUNDS | | | | | | | | | | | | | | | | |
| $NH_4Cl$ | 1 | | | | | | | | 1 | 1 | | | | | | |
| KCl | | 1 | | | | | | 2 | | | 0.5 | 1.5 | | | | |
| $(NH_4)_2SiF_6$ | | | 1 | | | | | | 1 | | | | 1.5 | 00.05 | | |
| $MgSiF_6$ | | | | 1 | | | | | | | 0.5 | | | | | |
| $AlNH_4(SO_4)_2$ | | | | | 1 | | | | | | 0.5 | | | | 0.5 | 1.5 |
| $MgSO_4$ | | | | | | 3 | | | | | | | | 3 | | |
| $Al_2(SO_4)_3$ | | | | | | | 1 | | | | | | | | 0.5 | |
| Set Time (Min) | 5 | 5 | 5 | 5 | 5 | 5 | 5 | 5 | 5 | 5 | 5 | 5 | 5 | 5 | 5 | 5 |
| % Increase | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 | 0.10 |

| Example | 97 | 98 | 99 | 100 |
|---|---|---|---|---|
| ACID COMPOUNDS | | | | |
| Boric | | | | |
| Phosphoric | | | | |
| Citric | | | | |
| Na Citric | | | | |
| $Na_3$ Citric | | | | |
| Tartaric | | | | |
| Oxalic | | | | |
| Sulfuric | | | | |
| Acetic | | | | |
| Formic | | | | |
| Ascorbic | | | | |
| Malic | | | | |
| Aspartic | | | | |
| COMPOUNDS | | | | |
| $NH_4Cl$ | | | | 0.05 |
| KCl | | | | |
| $(NH_4)_2SiF_6$ | | | | |
| $MgSiF_6$ | | | | |
| $AlNH_4(SO_4)_2$ | 0.05 | 0.3 | 0.1 | 0.5 |
| $MgSO_4$ | | | | |
| $Al_2(SO_4)_3$ | | | | |

-continued

| | | | | |
|---|---|---|---|---|
| Set Time (Min) | 2.5 | 2 | 7 | 1.5 |
| % Increased | 0.10 | 0.10 | 0.10 | 0.10 |

There are additionally occasions whereby dust is not a problem and larger amount of gypsum are needed for casts for figurines and the like. Our multi-part composition is certainly desirable for those.

The same proportion of compounds and acids are used for these large amounts of the gypsum and water components. They are supplied to the user in large containers and the user uses the traditional scoop and containers to mix the gypsum and water components to prepare the casting composition.

Therefore, it should be recognized that, while the invention has been described in relation to a preferred embodiment thereof, those skilled in the art may develop a wide variation of structural details without departing from the principles of the invention. Accordingly, the claims are construed to cover all equivalents falling within the scope and the spirit of the invention.

I claim:

1. A multi-part aqueous gypsum dental casting composition comprising:
   a first gypsum composition;
   a second water composition;
   at least two acids selected from the group consisting of oxalic acid, boric acid, phosphoric acid, citric acid, sodium citric acid, tri-sodium citric acid, tartaric acid, sulfuric acid, acetic acid, formic acid, malic acid, ascorbic acid, aspartic acid and mixtures thereof
   said first and second compositions being maintained separately and mixed when the casting is to be prepared; and
   said at least two acids being mixed in the gypsum and/or water compositions.

2. The dental casting composition of claim 1 wherein the composition contains dissolved in said water said at least two acids.

3. The dental casting composition of claim 2 wherein the two acids are boric acid and either phosphoric acid or trisodium citric acid.

4. The dental casting composition of claim 1 wherein the composition further comprises a compound selected from the group consisting of ammonium chloride, potassium chloride, ammonium fluorosilicate, magnesium fluorosilicate, magnesium sulfate, magnesium aluminum sulfate, aluminum sulfate, aluminum ammonium sulfate, and non-reactive mixtures thereof; and said compound being mixed in the gypsum and/or water compositions.

5. The dental casing composition of claim 4 wherein there are 0.2 to 12 parts by weight of aluminum ammonium sulfite, 0.2 to 12 parts by weight of boric acid, and 0.2 to 12 parts by weight of phosphoric acid or tri-sodium citric acid.

6. A gypsum dental casting water component container comprising 20 to 40 parts by weight of water for every 100 parts by weight of gypsum to be reacted with said water, and dissolved in said water 0.2 to 12 parts by weight of aluminum ammonia sulfate and 0.2 to 18 parts of a mixture of boric acid, and either phosphoric acid or tri-sodium citric acid.

7. A dosage size gypsum dental casting container having separate first and second compartments sealed from each other;
   said first compartment containing 100 parts by weight gypsum
   said second compartment containing 20 to 40 parts by weight of water;
   a total of 0.2 to 12 parts by weight of a compound being mixed with either or both the gypsum and water, said compound being selected from the group consisting of ammonium chloride, potassium chloride, ammonium fluorosilicate, magnesium fluorosilicate, magnesium sulfate, magnesium aluminum sulfate, aluminum sulfate, aluminum ammonium sulfate, and non-reactive mixtures thereof;
   a total of 0.2 to 18 parts by weight of at least two acids being mixed with either or both the gypsum and water and said at least two acids being selected from the group consisting of oxalic acid, boric acid, phosphoric acid, citric acid, sodium citric acid, tri-sodium citric acid, tartaric acid, sulfuric acid, acetic acid, formic acid, malic acid, ascorbic acid and aspartic acid.

8. The dosage size gypsum dental casting container of claim 7 wherein the second compartment contains boric acid, and either phosphoric acid or the tri-sodium citric acid as the acid; and contains aluminum ammonium sulfate as the compound.

9. A multi-part aqueous gypsum casting composition comprising: 100 parts by weight of a gypsum composition; 20 to 40 parts by weight of a water composition;
   0.2 to 12 parts by weight of a compound selected from the group consisting of ammonium chloride, potassium chloride, ammonium fluorosilicate, magnesium fluorosilicate, magnesium sulfate, magnesium aluminum sulfate, aluminum sulfate, aluminum ammonium sulfate, and non-reactive mixtures thereof;
   0.2 to 18 parts by weight of at least one acid selected from the group consisting of boric acid, phosphoric acid, tri-sodium citric acid and mixtures thereof;
   said gypsum and water compositions being maintained separately and mixed when the casting is to be prepared; and
   said compound or said acids being mixed with either or both the gypsum or water compositions prior to the water composition being mixed with the gypsum composition.

10. The gypsum casting composition of claim 9 wherein said compound is aluminum ammonium sulfate and said acid is a mixture of boric acid, and either phosphoric or tri-sodium citric acid.

11. The gypsum casting composition of claim 9 wherein there are at least two acids.

* * * * *